United States Patent [19]

Talebian et al.

[11] Patent Number: 4,956,459
[45] Date of Patent: Sep. 11, 1990

[54] PLATINUM COMPOUNDS SUITABLE FOR USE AS PHARMACEUTICALS

[75] Inventors: Abdolhossen Talebian, Herndon; Dianna C. Green, Falls Church, both of Va.; Charles F. Hammer, Washington, D.C.; Philip S. Schein, Bryn Mawr, Pa.

[73] Assignee: Georgetown University, Washington, D.C.

[21] Appl. No.: 143,763

[22] Filed: Jan. 14, 1988

Related U.S. Application Data

[63] Continuation-in-part of Ser. No. 74,600, Jul. 17, 1987, abandoned.

[51] Int. Cl.$^5$ .................... A61K 31/28; A61K 31/70; C07H 23/00
[52] U.S. Cl. .................... 536/121; 536/18.7; 536/22; 536/55; 536/122; 536/55.2; 514/23; 424/649
[58] Field of Search .................... 424/649; 536/18.7, 22, 536/55, 55.2, 121, 122; 514/23

[56] References Cited

U.S. PATENT DOCUMENTS

| | | | |
|---|---|---|---|
| 4,053,587 | 10/1977 | Davidson et al. | 424/649 |
| 4,200,583 | 4/1980 | Kidani et al. | 536/55 |
| 4,284,579 | 8/1981 | Meischen et al. | 424/649 |
| 4,536,571 | 8/1985 | Stockel et al. | 536/22 |
| 4,551,524 | 11/1985 | Kidani | 536/121 |
| 4,571,335 | 2/1986 | Taylor et al. | 424/649 |
| 4,575,550 | 3/1986 | Totani | 536/121 |
| 4,587,331 | 5/1986 | Hlavka et al. | 536/55 |
| 4,673,754 | 6/1987 | Smith et al. | 536/121 |
| 4,696,918 | 9/1987 | Stoddart et al. | 536/121 |
| 4,703,115 | 10/1987 | Hlavka et al. | 536/55 |
| 4,786,725 | 11/1988 | Amundsen et al. | 536/121 |

FOREIGN PATENT DOCUMENTS

| | | | |
|---|---|---|---|
| 059911 | 9/1982 | European Pat. Off. | 514/23 |
| 0167071 | 1/1986 | European Pat. Off. | |
| 0186085 | 7/1986 | European Pat. Off. | |
| 284197 | 9/1988 | European Pat. Off. | |
| 56-103192 | 8/1981 | Japan | 536/55 |

OTHER PUBLICATIONS

O. Gandolfi et al., "Aminomalonato(1,2-Diaminocyclohexane)Platinum(II)," *Inorganica Chimica Acta*, vol. 135, pp. 27–31, 1987.

M. P. Hacker et al., "Water-soluble N-Substituted Iminodiacetato(1,2-Diaminocyclohexane)-Platinum (II) Complexes as Potential Antitumor Agents," *Cancer Research*, vol. 46, pp. 6250–6254, 1986.

L. A. Zwelling, "Cisplatin and New Platinum Analogs," *Cancer Chemotherapy* 7, Ch. 8, pp. 105–122, 1985.

Gandolfi et al.; Inorganica Chimica Acta, 80:103–106, (1983).

Tobe et al.; Journal of Clinical Hematology and Oncology, 7(1):114–137, (1977).

Thiel et al.; Chemical Abstracts, 100:44337c, (1984).

Nagel et al.; Chemical Abstracts, 105:79243z, (1986).

Tsubomura et al.; Chemical Abstracts, 105:191536y, (1986).

Kolar et al.; Chemical Abstracts, 105:209336v, (1986).

*Primary Examiner*—Ronald W. Griffin
*Assistant Examiner*—Nancy S. Carson
*Attorney, Agent, or Firm*—Wegner & Bretschneider

[57] ABSTRACT

Compounds of the formula:

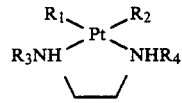

wherein each of $R_1$ and $R_2$ is independently selected from the group consisting of halogen, hydroxy, or mono carboxylic acid or $R_1$ and $R_2$ together is a multifunctional carboxylic acid residue which forms a ring with the platinum atom through two oxygens of said multifunctional carboxylic acid; $R_3$ is a deoxy mono or disaccharide or a derivative thereof; and $R_4$ is selected from the group consisting of hydrogen, $C_{1-4}$-alkyl, phenyl, benzyl, substituted phenyl or substituted benzyl, wherein substituents are selected from the group consisting of halogen, nitro, $C_{1-2}$-alkoxy, carboxy, carbony ester or phenyl or a pharmaceutically acceptable salt thereof are disclosed. Compositions containing these compounds and methods using these compounds are also discussed.

9 Claims, No Drawings

PLATINUM COMPOUNDS SUITABLE FOR USE AS PHARMACEUTICALS

This application is a continuation-in-part of Ser. No. 074,600, filed Jul. 17, 1987, abandoned.

BACKGROUND OF THE INVENTION

Platinum anti-cancer agents are known in the literature. One of the most well publicized of the platinum anti-cancer agents is cis-diammine-dichloroplatinum (II), also known as cis-DDP and cisplatin. A discussion of cisplatin and its usefulness in the treatment of various types of cancer, such as testicular carcinoma, bladder cancer, ovarian cancer, and head and neck cancer can be found in Zwelling, *Cancer Chemotherapy*, pp. 105-122 (1985).

Problems arise when such platinum agents are used in cancer treatment however. The toxicity of platinum to the bone marrow and kidneys precludes large sized dosages which can, in effect, render such treatment ineffective. Also, the overall desirability of and confidence in chemotherapy based upon known platinum active ingredients is decreased due to the drastic consequences to bone marrow and kidneys of the use of toxic levels of platinum.

SUMMARY OF THE INVENTION

The present invention is directed toward platinum anticancer agents having increased water solubility. Such an increase in water solubility aids the body in passing the platinum out of the system, thus preserving healthy bone marrow and kidneys. The water solubility of the platinum anti-cancer agents is enhanced by the presence of a mono or disaccharide group on the platinum active ingredient compound.

Pharmaceutical compositions containing the active ingredient and methods of treating carcinoma by administering said compositions to patients suffering from carcinoma are also discussed.

DETAILED DESCRIPTION OF THE INVENTION

In a first aspect of the present invention, there is provided a compound of the formula:

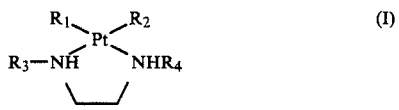

wherein each of $R_1$ and $R_2$ is independently selected from the group consisting of halogen, hydroxy, or mono carboxylic acid or $R_1$ and $R_2$ together is a multifunctional carboxylic acid residue which forms a ring with the platinum atom through two oxygens of said multifunctional carboxylic acid; $R_3$ is a deoxy mono or disaccharide or a derivative thereof; and $R_4$ is selected from the group consisting of hydrogen, $C_{1-4}$-alkyl, phenyl, benzyl, substituted phenyl or substituted benzyl, wherein substituents are selected from the group consisting of halogen, nitro, $C_{1,2}$-alkoxy, carboxy, carbonyl ester or phenyl
or a pharmaceutically acceptable salt thereof.

As a mono or disaccharide of the present invention there is contemplated any conventional mono or disaccharide. The saccharides may be in pyranosyl or furanosyl form. Preferred form for the saccharides of the present invention is the pyranosyl form. Exemplary monosaccharides are glucose, mannose, galactose, sedoheptulose, sorbose, fructose, ribulose, and xylulose. Exemplary disaccharides are sucrose, lactose, cellobiose, maltose and isomaltose. A deoxy form of the mono or disaccharide is used in the present invention.

By carbonyl ester there is contemplated a group of the formula —CO—O—R′, wherein R′ is $C_{1-4}$-alkyl, phenyl or benzyl.

As said derivative of the mono or disaccharides there may be mentioned sugar alcohols, deoxy sugars, glyconic acids, glycuronic acids, glycosides, acetyl substituted, amino substituted, N-acetylamino substituted, and the like. Combinations of the various aforementioned substituents on one saccharide are also contemplated. For example, a 6-deoxy1,2,3,4-di-O-isopropylidene-alpha-D-6-galactopyranosyl saccharide moiety is contemplated by the present invention.

As a mono carboxylic acid of the present invention there is contemplated any natural or synthetic mono carboxylic acid. Exemplary of such carboxylic acids (formula RCOOH) are alkyl, alkenyl, alkynyl, cycloalkyl, and the like. These "R" groups may be substituted or unsubstituted with biologically compatible substituents such as lower alkyl, hydroxy and the like.

As a multifunctional carboxylic acid residue which forms a ring with the platinum atom through two oxygens of said multifunctional carboxylic acid of the present invention there is contemplated a mono or polycyclic ring system. Exemplary of such multifunctional carboxylic acid residues are residues of the formulae:

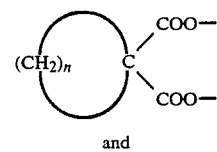

and

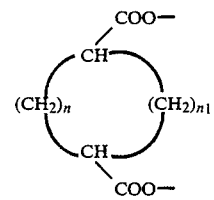

The value of n is a whole number between 0 and 6 and the value of $n_1$ is 0 or 1. These residues may be substituted or unsubstituted with biologically compatible substituents such as lower alkyl, hydroxy and the like.

The second ring, i.e. the ring which does not contain the carboxylic acid moieties may also be heterocyclic five or six membered rings having one or more of either nitrogen, oxygen or sulfur or a combination thereof. Exemplary of such rings are furan, pyran, piperidine, and the like.

As a pharmaceutically acceptable salt there is contemplated any salt that is safe for ingestion or injection and that is biologically inert, and hence does not interfere with the active ingredient. As such pharmaceutically acceptable salts may be mentioned sulfates, phosphates and the like.

A preferred embodiment of the present invention is a compound of formula (I), wherein $R_1$ and $R_2$ are halogen. A more preferred embodiment of the invention involves a compound of formula (I), wherein $R_1$ and $R_2$ are chlorine.

Another preferred embodiment of the present invention involves a compound of formula (I), wherein $R_1$ and $R_2$ are hydroxy.

A further preferred embodiment of the present invention involves a compound of formula (I), wherein $R_1$ and $R_2$ are mono carboxylic acids.

A still further preferred embodiment of the present invention is a compound of formula (I), wherein $R_1$ and $R_2$ together form a group of the formula:

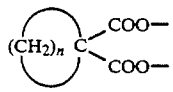

Yet another preferred embodiment of the invention is a compound of formula (I), wherein $R_1$ and $R_2$ together form a group of the formula:

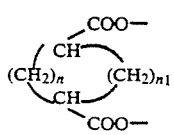

Another preferred embodiment of the present invention involves a compound of formula (I), wherein $R_3$ is a mono or disaccharide or derivative thereof selected from the group consisting of glucose, galactose, mannose, glucosamine and galactosamine and derivatives thereof.

A further preferred embodiment of the present invention involves a compound of formula (I), wherein said pharmaceutically acceptable salt is a sulfate salt.

In accordance with the present invention a pharmaceutical composition for the treatment of ailments consisting of testicular cancer, cancer of the head and neck cancer, cancer of the bladder and cancer of the colon comprising a pharmaceutically effective amount of a compound of the formula (I) and a pharmaceutically acceptable carrier therefor.

The active ingredient is admixed with a pharmaceutically acceptable solid or liquid carrier to allow oral, parenteral, intramuscular or intravenous administration of effective amounts of the pharmaceutical.

As a dosage form for oral delivery there is contemplated any dosage form capable of being delivered orally. That is, tablets, coated tablets, capsules, caplets or any other oral dosage form are contemplated by the present invention.

As said pharmaceutically acceptable inert ingredients there are contemplated pharmaceuticals, carriers, excipients, fillers, etc. which do not interfere with the anticancer activity of said compound.

Fillers such as clays or siliceous earth may be utilized if desired to adjust the size of the dosage form. Further ingredients such as excipients and carriers may be necessary to impart the desired physical properties of the dosage form. Such physical properties are, for example, release rate, texture and size of the dosage form. Examples of excipients and carriers useful in oral dosage forms are waxes such as beeswax, castor wax glycowax and carnauba wax, cellulose compounds such as methylcellulose, ethylcellulose, carboxymethylcellulose, cellulose acetate phthalate, hydroxypropylcellulose and hydroxypropylmethylcellulose, polyvinyl chloride, polyvinyl pyrrolidone, stearyl alcohol, glycerin monostearate, methacrylate compounds such as polymethacrylate, methyl methacrylate and ethylene glycol dimethacrylate, polyethylene glycol and hydrophilic gums.

As an intraperitoneal, intramuscular or intravenous dosage form there is contemplated any dosage form safe for injection purposes and capable of delivering the active platinum containing compound to a patient suffering from ailments consisting of testicular cancer, cancer of the ovary, head and neck cancer, cancer of the bladder and cancer of the colon. Exemplary of such a solution is an isotonic solution. An isotonic solution of the invention may contain in addition to said compound, water and salt, also conventional ingredients such as glucose.

A preferred composition of the present invention is a composition containing a compound of formula (I), wherein $R_1$ and $R_2$ are halogen. A more preferred composition of the invention involves composition containing a compound of formula (I), wherein $R_1$ and $R_2$ are chlorine.

Another preferred composition of the present invention involves a composition containing a compound of formula (I), wherein $R_1$ and $R_2$ are hydroxy.

A further preferred composition of the present invention involves a composition containing a compound of formula (I), wherein $R_1$ and $R_2$ are mono carboxylic acids.

A still further preferred composition of the present invention is a composition containing a compound of formula (I), wherein $R_1$ and $R_2$ together form a group of the formula:

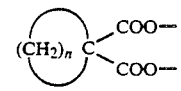

Yet another preferred composition of the invention is a composition containing a compound of formula (I), wherein $R_1$ and $R_2$ together form a group of the formula:

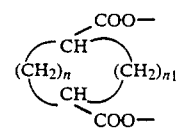

Another preferred composition of the present invention involves a composition containing a compound of formula (I), selected from the group consisting of glucose, galactose, mannose, glucosamine and galactosamine and derivatives thereof.

A further preferred composition of the present invention involves a composition containing a compound of formula (I), wherein said pharmaceutically acceptable salt is a sulfate salt.

Further in accordance with the present invention there is provided a method for the treatment of ailments consisting of testicular cancer, cancer of the ovary head and neck cancer, cancer of the bladder and cancer of the colon comprising administration of a pharmaceutically effective amount of a compound of the formula (I) and a pharmaceutically acceptable carrier therefor to a patient suffering from said ailments.

The administration can occur through oral, intraperitoneal, intramuscular and intravenous routes. Therapeutic treatment profiles can be arranged to administer the compound in accordance with the need of the patient. The need of the patient is dependent on typical factors such as the advancement of the disease, the patient's age, general health, and the like. Daily, weekly, or dosing every two or three weeks are exemplary of possible treatment protocols. With respect to intravenous administration, the compound could be administered constantly. Periods up to 7 days are exemplary of possible intravenous treatment protocols.

Regardless of mode of administration, an exemplary dose of the active compound is from about 1 to about 1000 mg per m$^2$ body surface area of a patient. A preferred dosage of the active compound involves the administration of about 10 to about 200 mg per m$^2$ body surface area of a patient. A more preferred dosage of the active compound involves the administration of about 50 to about 150 mg per m$^2$ body surface area of a patient.

A preferred method of the present invention is a method of administering a compound of formula (I), wherein $R_1$ and $R_2$ are halogen. A more preferred method of the invention involves a method of administering a compound of formula (I), wherein $R_1$ and $R_2$ are chlorine.

Another preferred method of the present invention involves a method of administering a compound of formula (I), wherein $R_1$ and $R_2$ are hydroxy.

A further preferred method of the present invention involves a method of administering a compound of formula (I), wherein $R_1$ and $R_2$ are mono carboxylic acids.

A still further preferred method of the present invention is a method of administering a compound of formula (I), wherein $R_1$ and $R_2$ together form a group of the formula:

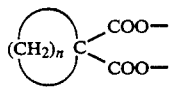

Yet another preferred method of the invention is a method of administering a compound of formula (I), wherein $R_1$ and $R_2$ together form a group of the formula:

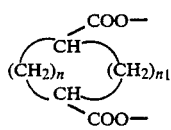

Another preferred method of the present invention involves a method of administering a compound of formula (I), wherein $R_3$ is a mono or disaccharide or derivative thereof selected from the group consisting of glucose, galactose, mannose, glucosamine and galactosamine and derivatives thereof.

A further preferred method of the present invention involves a method of administering a compound of formula (I), wherein said pharmaceutically acceptable salt is a sulfate salt.

The compounds of formula (I) of the present invention may be prepared according to the following reaction scheme:

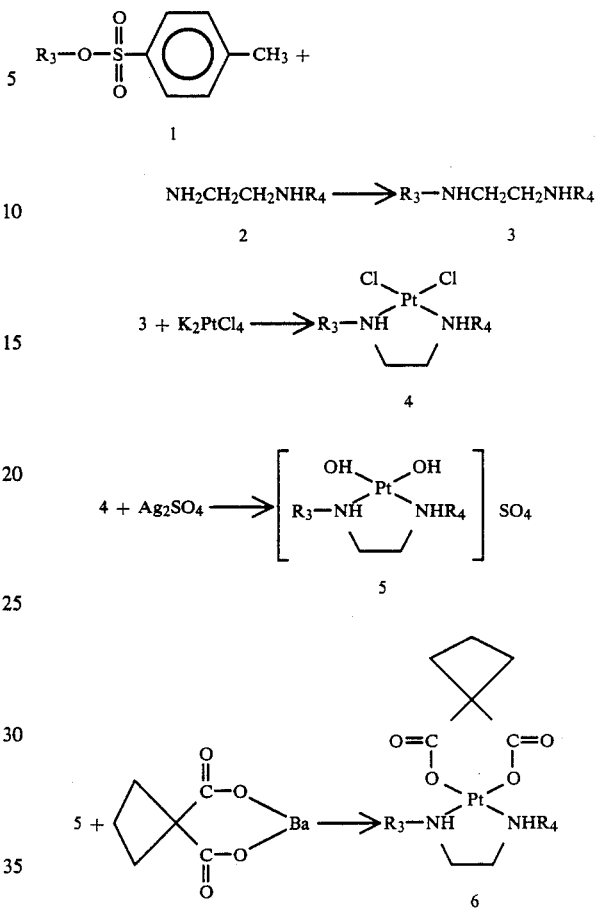

Compound 4, 5 and 6 are compounds of the present invention.

If any saccharide-hydroxy blocking groups are present in the deoxy mono or disaccharide sugar used in the present invention, such blocking groups may be removed by the addition of either 6-N HCl or aqueous CF$_3$COOH. This blocker removal can be accomplished either before or after the addition of the platinum compound.

The following are exemplary of the present invention.

EXAMPLE I 7.24 mmol of 1,2:3,4-di-O-isopropylidene-6-O-p-tolyl-sulfonyl-alpha-D-galactopyranose is added to 20 ml ethylenediammine and is stirred vigorously at 100 degrees celsius for 3 hours. Excess ethylenediammine is removed under reduced pressure and the resulting semi-solid residue is partitioned between CH$_2$Cl$_2$ and 10% NaHCO$_3$. The CH$_2$CL$_2$ layer is backwashed with water, is dried over Na$_2$SO$_4$ and is evaporated to dryness. An intermediate of formula 3 is obtained upon recrystallization from ethylether.

0.00165 mmol of this product are then added to a filtered solution of 0.00182 mmol potassium tetrachloroplatinate(II) in 10 ml water. The mixture is stirred at room temperature and the resulting precipitate is filtered off. The filtrate is then washed with water, methanol and acetone. Purification is continued through drying over P$_2$O$_5$ in vacuo to yield a product of formula 4.

100 mg of the product is dissolved in 10 ml of 6-N HCL and is heated to 80 degrees celsius. The solution is then cooled and freeze dried. The solid residue is redissolved in 10 ml of water and subsequently is lypholized to yield cis-dichloro-[N-(6-deoxy-alpha-D-galactopyranosyl)-1,2-ethylenediammine-N,N-]platinum(II).

This solution is then suspended in 5 ml of water and silver sulfate which is dissolved in 30 ml of water is added. The mixture is protected from light and is stirred at room temperature for 24 hours. Barium sulfate is then filtered off and the filtrate is evaporated to dryness under reduced pressure to yield a product of formula 5.

An equivalent of a barium salt of 1,1cyclobutanedicarboxylic acid is then added to the product to yield a product of formula 6.

EXAMPLE II

The product of formula 4 of Example I is admixed with an isotonic solution to produce a dosage form suitable for intravenous administration. 130 mg/m$^2$ body surface area of a patient is administered to said patient through intravenous administration over a period of 24 hours.

The product of formula 5 of Example I is admixed with an isotonic solution to produce a dosage form suitable for intravenous administration. 110 mg/m$^2$ body surface area of a patient is administered to said patient through intravenous administration over a period of 24 hours.

The product of formula 6 of Example I is admixed with an isotonic solution to produce a dosage form suitable for intravenous administration. 80 mg/m$^2$ body surface area of a patient is administered to said patient through intravenous administration over a period of 24 hours.

EXAMPLE III 7.24 mmol of 6-O-p-tolylsulfonylglucopyranose is added to 20 ml ethylenediammine and is stirred vigorously at 100 degrees celsius for 3 hours. Excess ethylenediammine is removed under reduced pressure and the resulting semi-solid residue is partitioned between CH$_2$Cl$_2$ and 10% NaHCO$_3$. The CH$_2$Cl$_2$ layer is backwashed with water, is dried over Na$_2$SO$_4$ and is evaporated to dryness. An intermediate of formula 3 is obtained upon recrystallization from ethylether.

0.00165 mmol of this product are then added to a filtered solution of 0.00182 mmol potassium tetrachloroplatinate(II) in 10 ml water. The mixture is stirred at room temperature and the resulting precipitate is filtered off. The filtrate is then washed with water, methanol and acetone. Purification is continued through drying over P$_2$O$_5$ in vacuo to yield a product of formula 4.

This solution is then suspended in 5 ml of water and silver sulfate which is dissolved in 30 ml of water is added. The mixture is protected from light and is stirred at room temperature for 24 hours. Barium sulfate is then filtered off and the filtrate is evaporated to dryness under reduced pressure to yield a product of formula 5.

An equivalent of a barium salt of 1,1-cyclobutanedicarboxylic acid is then added to the product to yield a product of formula 6.

EXAMPLE IV

The product of formula 4 of Example III is admixed with hydroxypropylcellulose to produce a dosage form suitable for oral administration. 100 mg/m$^2$ body surface area of a patient is administered to said patient through oral administration daily.

The product of formula 5 of Example III is admixed with hydroxypropylcellulose to produce a dosage form suitable for oral administration. 150 mg/m$^2$ body surface area of a patient is administered to said patient through oral administration daily.

The product of formula 6 of Example III is admixed with hydroxypropylcellulose to produce a dosage form suitable for oral administration. 70 mg/m$^2$ body surface area of a patient is administered to said patient through oral administration daily.

EXAMPLE V 7.24 mmol of 6-O-p-tolylsulfonyl-alpha-D-mannopyranose is added to 20 ml ethylenediammine and is stirred vigorously at 100 degrees celsius for 3 hours. Excess ethylenediammine is removed under reduced pressure and the resulting semi-solid residue is partitioned between CH$_2$Cl$_2$ and 10% NaHCO$_3$. The CH$_2$Cl$_2$ layer is backwashed with water, is dried over Na$_2$SO$_4$ and is evaporated to dryness. An intermediate of formula 3 is obtained upon recrystallization from ethylether.

0.00165 mmol of this product are then added to a filtered solution of 0.00182 mmol potassium tetrachloroplatinate(II) in 10 ml water. The mixture is stirred at room temperature and the resulting precipitate is filtered off. The filtrate is then washed with water, methanol and acetone. Purification is continued through drying over P$_2$O$_5$ in vacuo to yield a product of formula 4.

This solution is then suspended in 5 ml of water and silver sulfate which is dissolved in 30 ml of water is added. The mixture is protected from light and is stirred at room temperature for 24 hours. Barium sulfate is then filtered off and the filtrate is evaporated to dryness under reduced pressure to yield a product of formula 5.

An equivalent of a barium salt of 1,1-cyclobutanedicarboxylic acid is then added to the product to yield a product of formula 6.

EXAMPLE VI

The product of formula 4 of Example VI is admixed with an isotonic solution to produce a dosage form suitable for intraperitoneal administration. 150 mg/m$^2$ body surface area of a patient is administered to said patient through intraperitoneal administration every 3 weeks.

The product of formula 5 of Example VI is admixed with an isotonic solution to produce a dosage form suitable for intraperitoneal administration. 60 mg/m$^2$ body surface area of a patient is administered to said patient through intraperitoneal administration every 3 weeks.

The product of formula 6 of Example VI is admixed with an isotonic solution to produce a dosage form suitable for intraperitoneal administration. 110 mg/m$^2$ body surface area of a patient is administered to said patient through intraperitoneal administration every 3 weeks.

EXAMPLE VII 7.24 mmol of N-acetyl-6-O-p-tolylsulfonyl-alpha-Dgalactosaminepyranose is added to 20 ml ethylenediammine and is stirred vigorously at 100 degrees celsius for 3 hours. Excess ethylenediammine is removed under reduced pressure and the resulting semi-solid residue is partitioned between CH$_2$Cl$_2$ and 10%

NaHCO$_3$. The CH$_2$Cl$_2$ layer is backwashed with water, is dried over Na$_2$SO$_4$ and is evaporated to dryness. An intermediate of formula 3 is obtained upon recrystallization from ethylether.

0.00165 mmol of this product are then added to a filtered solution of 0.00182 mmol potassium tetrachloroplatinate(II) in 10 ml water. The mixture is stirred at room temperature and the resulting precipitate is filtered off. The filtrate is then washed with water, methanol and acetone. Purification is continued through drying over P$_2$O$_5$ in vacuo to yield a product of formula 4.

This solution is then suspended in 5 ml of water and silver sulfate which is dissolved in 30 ml of water is added. The mixture is protected from light and is stirred at room temperature for 24 hours. Barium sulfate is then filtered off and the filtrate is evaporated to dryness under reduced pressure to yield a product of formula 5.

An equivalent of a barium salt of 1,1-cyclobutanedicarboxylic acid is then added to the product to yield a product of formula 6.

EXAMPLE VIII

The product of formula 4 of Example VII is admixed with an isotonic solution to produce a dosage form suitable for intramuscular administration. 50 mg/m$^2$ body surface area of a patient is administered to said patient through intramuscular administration daily.

The product of formula 5 of Example VII is admixed with an isotonic solution to produce a dosage form suitable for intramuscular administration. 140 mg/m$^2$ body surface area of a patient is administered to said patient through intramuscular administration daily.

The product of formula 6 of Example VII is admixed with an isotonic solution to produce a dosage form suitable for intramuscular administration. 90 mg/m$^2$ body surface area of a patient is administered to said patient through intramuscular administration daily.

EXAMPLE IX 7.24 mmol of N-acetyl-6-O-p-tolylsulfonyl-alpha-D-glucosaminepyranose is added to 20 ml ethylenediammine and is stirred vigorously at 100 degrees celsius for 3 hours. Excess ethylenediammine is removed under reduced pressure and the resulting semi-solid residue is partitioned between CH$_2$Cl$_2$ and 10% NaHCO$_3$. The CH$_2$Cl$_2$ layer is backwashed with water, is dried over Na$_2$SO$_4$ and is evaporated to dryness. An intermediate of formula 3 is obtained upon recrystallization from ethylether.

0.00165 mmol of this product are then added to a filtered solution of 0.00182 mmol potassium tetrachloroplatinate(II) in 10 ml water. The mixture is stirred at room temperature and the resulting precipitate is filtered off. The filtrate is then washed with water, methanol and acetone. Purification is continued through drying over P$_2$O$_5$ in vacuo to yield a product of formula 4.

This solution is then suspended in 5 ml of water and silver sulfate which is dissolved in 30 ml of water is added. The mixture is protected from light and is stirred at room temperature for 24 hours. Barium sulfate is then filtered off and the filtrate is evaporated to dryness under reduced pressure to yield a product of formula 5.

An equivalent of a sodium salt of acetic acid is then added to the product to yield a product of formula 6.

EXAMPLE X

The product of formula 4 of Example IX is admixed with glycerin monostearate to produce a dosage form suitable for oral administration. 70 mg/m$^2$ body surface area of a patient is administered to said patient through oral administration daily.

The product of formula 5 of Example IX is admixed with glycerin monostearate to produce a dosage form suitable for oral administration. 150 mg/m$^2$ body surface area of a patient is administered to said patient through oral administration daily.

The product of formula 6 of Example IX is admixed with glycerin monostearate to produce a dosage form suitable for oral administration. 170 mg/m$^2$ body surface area of a patient is administered to said patient through oral administration daily.

EXAMPLE XI 7.24 mmol of 6-O-p-tolylsulfonyl-alpha-D-galactopyranose is added to 20 ml ethylenediammine and is stirred vigorously at 100 degrees celsius for 3 hours. Excess ethylenediammine is removed under reduced pressure and the resulting semi-solid residue is partitioned between CH$_2$Cl$_2$ and 10% NaHCO$_3$. The CH$_2$Cl$_2$ layer is backwashed with water, is dried over Na$_2$SO$_4$ and is evaporated to dryness. An intermediate of formula 3 is obtained upon recrystallization from ethylether.

0.00165 mmol of this product are then added to a filtered solution of 0.00182 mmol potassium tetrachloroplatinate(II) in 10 ml water. The mixture is stirred at room temperature and the resulting precipitate is filtered off. The filtrate is then washed with water, methanol and acetone. Purification is continued through drying over P$_2$O$_5$ in vacuo to yield a product of formula 4.

This solution is then suspended in 5 ml of water and silver sulfate which is dissolved in 30 ml of water is added. The mixture is protected from light and is stirred at room temperature for 24 hours. Barium sulfate is then filtered off and the filtrate is evaporated to dryness under reduced pressure to yield a product of formula 5.

An equivalent of a barium salt of propionic acid is then added to the product to yield a product of formula 6.

EXAMPLE XII

The product of formula 4 of Example XI is admixed with an isotonic solution to produce a dosage form suitable for intraperitoneal administration. 150 mg/m$^2$ body surface area of a patient is administered to said patient through intraperitoneal administration weekly.

The product of formula 5 of Example XI is admixed with an isotonic solution to produce a dosage form suitable for intraperitoneal administration. 60 mg/m$^2$ body surface area of a patient is administered to said patient through intraperitoneal administration weekly.

The product of formula 6 of Example XI is admixed with an isotonic solution to produce a dosage form suitable for intraperitoneal administration. 110 mg/m$^2$ body surface area of a patient is administered to said patient through intraperitoneal administration weekly.

EXAMPLE XIII 7.24 mmol of 1,2:3,4-di-O-isopropylidene-6-O-p-tolylsulfonyl-alpha-D-glucofuranose is added to 20 ml ethylenediammine and is stirred vigorously at 100 degrees celsius for 3 hours. Excess ethylenediammine is removed under reduced pressure and the resulting semi-solid residue is partitioned between CH$_2$Cl$_2$ and 10% NaHCO$_3$. The CH$_2$Cl$_2$ layer is backwashed with water, is dried over Na$_2$SO$_4$ and is evaporated to dryness. An intermediate of formula 3 is obtained upon recrystallization from ethylether.

0.00165 mmol of this product are then added to a filtered solution of 0.00182 mmol potassium tetrachloroplatinate(II) in 10 ml water. The mixture is stirred at room temperature and the resulting precipitate is filtered off. The filtrate is then washed with water, methanol and acetone. Purification is continued through drying over $P_2O_5$ in vacuo to yield a product of formula 4.

100 mg of the product is dissolved in 10 ml of 6-N HCl and is heated to 80 degrees celsius. The solution is then cooled and freeze dried. The solid residue is redissolved in 10 ml of water and subsequently is lypholized to yield cis-dichloro-[N-(6-deoxy-alpha-glucopyranosyl)-1,2-ethylenediammine]platinum(II).

This solution is then suspended in 5 ml of water and silver sulfate which is dissolved in 30 ml of water is added. The mixture is protected from light and is stirred at room temperature for 24 hours. Barium sulfate is then filtered off and the filtrate is evaporated to dryness under reduced pressure to yield a product of formula 5.

An equivalent of a barium salt of 1,1-cyclobutanedicarboxylic acid is then added to the product to yield a product of formula 6.

EXAMPLE XIV

The product of formula 4 of Example XIII is admixed with an isotonic solution to produce a dosage form suitable for intravenous administration. 130 mg/m$^2$ body surface area of a patient is administered to said patient through intravenous administration over a period of 24 hours.

The product of formula 5 of Example XIII is admixed with an isotonic solution to produce a dosage form suitable for intravenous administration. 100 mg/m$^2$ body surface area of a patient is administered to said patient through intravenous administration over a period of 24 hours.

The product of formula 6 of Example XIII is admixed with an isotonic solution to produce a dosage form suitable for intravenous administration. 80 mg/m$^2$ body surface area of a patient is administered to said patient through intravenous administration over a period of 24 hours.

EXAMPLES XV-XXX

Examples I-XVI are repeated substituting 1,2-isopropyldiammine for ethylenediamine to produce compounds wherein $R_4$ is methyl.

EXAMPLES XXXI-XLVI

Examples I-XVI are repeated substituting 1-phenylethylenediamine for ethylenediamine to produce compounds wherein $R_4$ is phenyl.

EXAMPLE XLVII

Cis-dichloro-[N-(6-deoxy-1,2:3,4-di-O-isopropylidene-alpha-D-6-galactopyranosyl)-1,2-ethylenediammine-N,N']-platinum(II) and cisplatin were tested against murine P388 leukemia. The murine P388 leukemia system is known to be sensitive to cisplatin. The leukemia was maintained intraperitoneally in female DBA/2 mice.

Prior to administration, each compound was dissolved in ethanol. The solutions were then adjusted to 5% ethanol, 95% sterile water.

Each compound was administered intraperitoneally to groups of CD2F$_1$ male mice on day 1 after intraperitoneal implantation of 1×10$^6$ P388 leukemia cells. P388 artileukemic activity for the compounds was assessed by mean survival days and percentage increased life span (% ILS).

% ILS is calculated as follows:

%ILS=(T-C)/C×100 wherein T is the mean survival days of the treated mice and C is the mean survival days of the untreated mice. The results of the experimentation are shown in the table.

TABLE 1

| Compound | Dose | % ILS | Mean Survival (days) |
|---|---|---|---|
| cisplatin | 10 mg/kg | 83 | 17.4 |
| invention | 150 mg/kg | 72 | 16.3 |

What is claimed is:

1. A compound of the formula:

$$\begin{array}{c} R_1 \diagdown \quad \diagup R_2 \\ Pt \\ R_3NH \diagup \quad \diagdown NHR_4 \\ \underline{\qquad\qquad} \end{array}$$

wherein each of $R_1$ and $R_2$ is independently selected from the group consisting of halogen, hydroxy, or mono carboxylic acid or $R_1$ and $R_2$ together is a multifunctional carboxylic acid residue which forms a ring with the platinum atom through two oxygens of said multifunctional carboxylic acid; $R_3$ is a deoxy mono or disaccharide or a derivative thereof; and $R_4$ is selected from the group consisting of hydrogen, $C_{1-4}$-alkyl, phenyl, benzyl, substituted phenyl or substituted benzyl, wherein substituents are selected from the group consisting of halogen, nitro, $C_{1-2}$-alkoxy, carboxy, carbonyl ester or phenyl
or a pharmaceutically acceptable salt thereof.

2. A compound of claim 1, wherein $R_1$ and $R_2$ are halogen.

3. A compound of claim 2, wherein $R_1$ and $R_2$ are chlorine.

4. A compound of claim 1, wherein $R_1$ and $R_2$ are hydroxy.

5. A compound of claim 1, wherein $R_1$ and $R_2$ are mono carboxylic acids.

6. A compound of claim 1, wherein $R_1$ and $R_2$ together form a group of the formula:

$$(CH_2)_n \diagup C \diagdown \begin{array}{c} COO- \\ COO- \end{array}$$

7. A compound of claim 1, wherein $R_1$ and $R_2$ together form a group of the formula:

$$\begin{array}{c} \diagup CH \diagdown \quad COO- \\ (CH_2)_n \quad (CH_2)_{n1} \\ \diagdown CH \diagup \\ \diagdown COO- \end{array}$$

wherein n is 0, 1, 2, 3, 4, 5 or 6 and $n_1$ is 0 or 1.

8. A compound of claim 1, wherein $R_3$ is a mono or disaccharide or derivative thereof selected from the group consisting of glucose, galactose, mannose, glucosamine and galactosamine and derivatives thereof.

9. A compound of claim 1, wherein said pharmaceutically acceptable salt is a sulfate salt.